(12) United States Patent
Dall'Oglio et al.

(10) Patent No.: US 8,441,637 B2
(45) Date of Patent: May 14, 2013

(54) METHOD AND DEVICE OF COMPENSATING SCATTERING LIGHT SIGNALS GENERATED BY LIGHT INTERACTION WITH PARTICLES OR BIOLOGICAL CELLS MOVING IN FLUID CURRENTS, SUCH AS IN FLOW CYTOMETRY

(75) Inventors: Stefano Dall'Oglio, Milan (IT); Giorgio Dall'Oglio, Milan (IT)

(73) Assignee: STRICTES S.r.l., Milan (IT)

( * ) Notice: Subject to any disclaimer, the term of this patent is extended or adjusted under 35 U.S.C. 154(b) by 239 days.

(21) Appl. No.: 12/992,433

(22) PCT Filed: May 15, 2009

(86) PCT No.: PCT/EP2009/055895
§ 371 (c)(1),
(2), (4) Date: Apr. 6, 2011

(87) PCT Pub. No.: WO2009/138482
PCT Pub. Date: Nov. 19, 2009

(65) Prior Publication Data
US 2011/0176131 A1    Jul. 21, 2011

(30) Foreign Application Priority Data
May 15, 2008 (IT) ............................. F12008A0095

(51) Int. Cl.
*G01N 21/00* (2006.01)
(52) U.S. Cl.
USPC ........................................................ 356/338
(58) Field of Classification Search .................. 356/337, 356/338
See application file for complete search history.

(56) References Cited

U.S. PATENT DOCUMENTS

| 3,527,542 | A | * | 9/1970 | Rader et al. .................... 356/244 |
| 4,522,494 | A | * | 6/1985 | Bonner ............................ 356/39 |
| 4,732,479 | A | | 3/1988 | Tanaka et al. |
| 5,534,999 | A | * | 7/1996 | Koshizuka et al. ........... 356/338 |
| 6,232,125 | B1 | | 5/2001 | Deka et al. |
| 6,417,920 | B1 | | 7/2002 | Shimaoka |
| 7,092,078 | B2 | | 8/2006 | Nagai et al. |
| 2002/0030815 | A1 | | 3/2002 | Ichijo |
| 2002/0041376 | A1 | | 4/2002 | Kurozumi et al. |
| 2007/0188737 | A1 | | 8/2007 | Fritz |
| 2011/0155927 | A1 | * | 6/2011 | Mitchell et al. ............ 250/459.1 |

FOREIGN PATENT DOCUMENTS

| EP | 0696731 | 2/1996 |
| JP | 5215662 | 8/1993 |

OTHER PUBLICATIONS

International Search Report for PCT/EP2009/055895 dated Sep. 16, 2009.

* cited by examiner

*Primary Examiner* — Roy M Punnoose
(74) *Attorney, Agent, or Firm* — Abelman, Frayne & Schwab

(57) ABSTRACT

A method and device of detecting a scattering light beam for tools measuring scattering signals produced by the interaction of solid microparticles, such as a biological cells moving with a high-intensity, focused light beam, capable of reducing the influence of the cell movement with respect to the optical axis of the illuminating beam, and improving the quality of the signal characterized by the recognition of the individual particle or cell, specifically in fluid currents, such as those used in flow cytometry are disclosed.

12 Claims, 6 Drawing Sheets

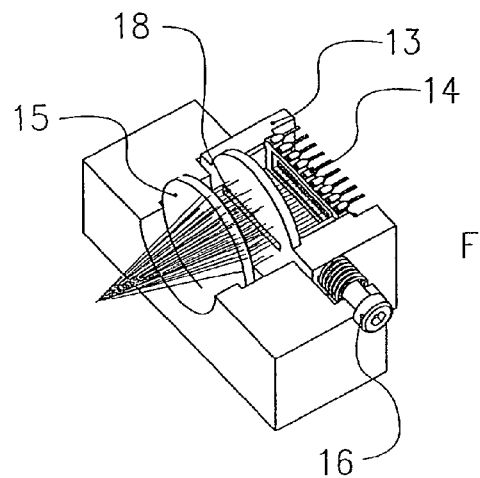
Fig. 2a
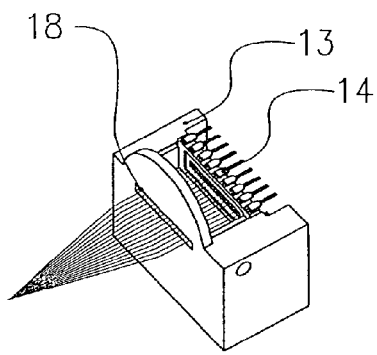
Fig. 2b
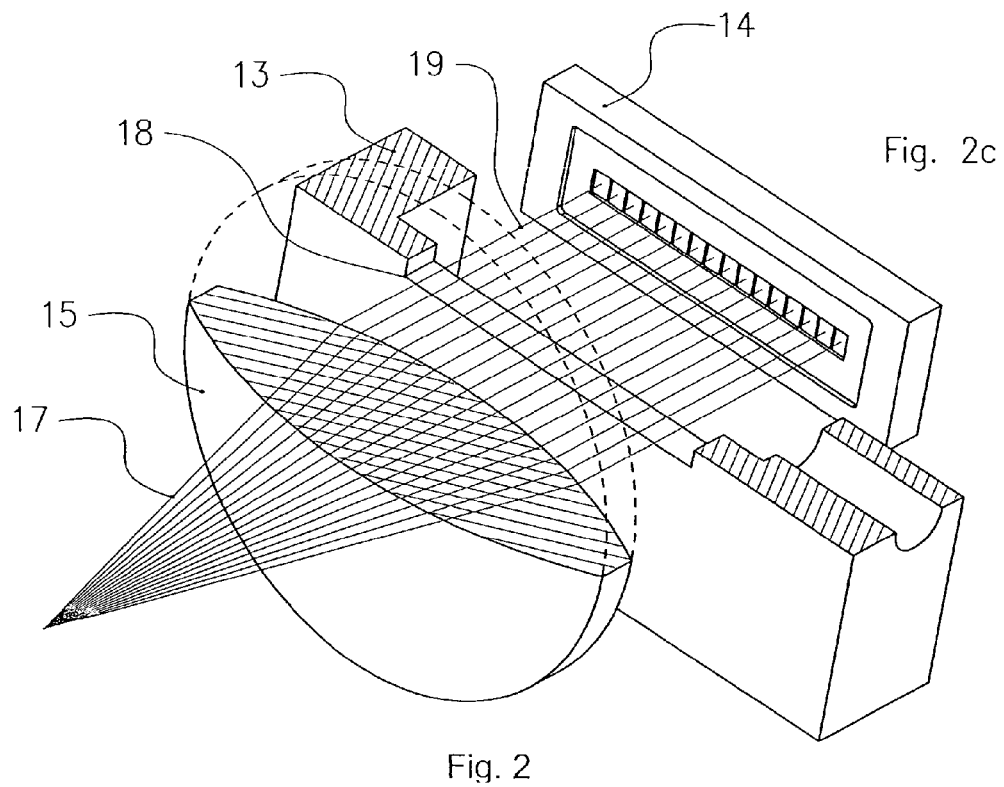
Fig. 2c
Fig. 2

US 8,441,637 B2

METHOD AND DEVICE OF COMPENSATING SCATTERING LIGHT SIGNALS GENERATED BY LIGHT INTERACTION WITH PARTICLES OR BIOLOGICAL CELLS MOVING IN FLUID CURRENTS, SUCH AS IN FLOW CYTOMETRY

CROSS REFERENCE TO RELATED APPLICATIONS

This application is a §371 of PCT/EP2009/055895, filed May 15, 2009, which claims priority from Italian Application No. FI2008A000095, filed May 15, 2008.

FIELD OF THE INVENTION

The present invention relates to the field of optical measurements on scattering lights used for recognizing even microscopic solid particles, such as for example blood cells, in biomedical apparatuses such as flow cytometers.

STATE OF THE ART

Detectors intended to provide information related to particle scattering according to certain dispersion angles are known. Some of these detectors of the prior art are protected by patents, among which U.S. Pat. No. 6,232,125 (Deka et al.) and U.S. Pat. No. 7,092,078 (Nagai et al.) are mentioned.

Said patents describe dedicated photoelectric detector devices which, in order to compensate for the signal reduction described by Mie's law, are characterized by an area which increases proportionally to the scattering angle: thereby the number of detector elements forming said devices is limited and the total angular resolution is poor.

The prior art does not describe methods and apparatuses which are characterized by a high angular resolution, such that in order to be reached, it requires the detectors to be centered on the optical axis of the light beam exiting from the flow cells. An apparatus of this type and a method related thereto, being the object of the present patent application for industrial invention, solve the technical problem of reducing the inaccuracies affecting said methods and apparatuses of the prior art.

Said inaccuracies are substantially of two types: the first is related to the tolerances of the components employed in said apparatuses; the second is related to the influence of external variables which, for example, may cause the light beam in cytometers to make tiny movements between examinations, movements caused by minimal differences in the value of some of said external variables such as, for example, injection pressure, viscosity and temperature of the sample under examination.

Therefore, it is the object of the present invention to suggest a new and more effective solution to the problem of aligning the high-resolution photoelectric detector—of special type, of conventional type, i.e. consisting of a simple linear array of photoelectric detectors—with the optical axis of the light beam exiting from the flow cell, while analyzing the scatter signal correlated to the individual particle, thus detecting the symmetry or the possible asymmetry thereof to the right and to the left of the illuminating beam.

Such a method allows the so-called "scattering signature" of individual cells to be recognized.

SUMMARY OF THE INVENTION

For the purpose illustrated above, a device shown in the present patent application has been implemented, characterized by the use of a photoelectric detector comprising a linear set of photo-detectors, generally known as "linear diode array". Such a detector may consist of silicon photodiodes, APD (Avalanche Photo Diodes) photodiodes, and other known types of photodiodes, such as CCDs, etc. Said linear diode array is characterized by high sensitivity and is able to accumulate the electric charges generated by the photons which illuminate the photosensitive material, transferring their energy and releasing electrons during the illumination time interval, thus operating in practice as integrator with a quantity Q of electric charges proportional to the quantity of incident photons.

Linear diode arrays with a number of photo-transducer elements from five to over one thousand are known and commercialized.

By way of non-limitative example, a detector of this type is the S4111-16Q/-16R model made by Hamamatsu Photonics K.K.—Solid State Division, which consists of 16 separate photodiodes, size 0.9×1.45 mm, with a 15.9×1.45 mm active area (including 0.1 mm gaps between diodes).

BRIEF DESCRIPTION OF THE DRAWINGS

FIGS. 2a, 2b and 2c show the parts forming the device according to the present invention.

DETAILED DESCRIPTION OF THE INVENTION

Figure 1:
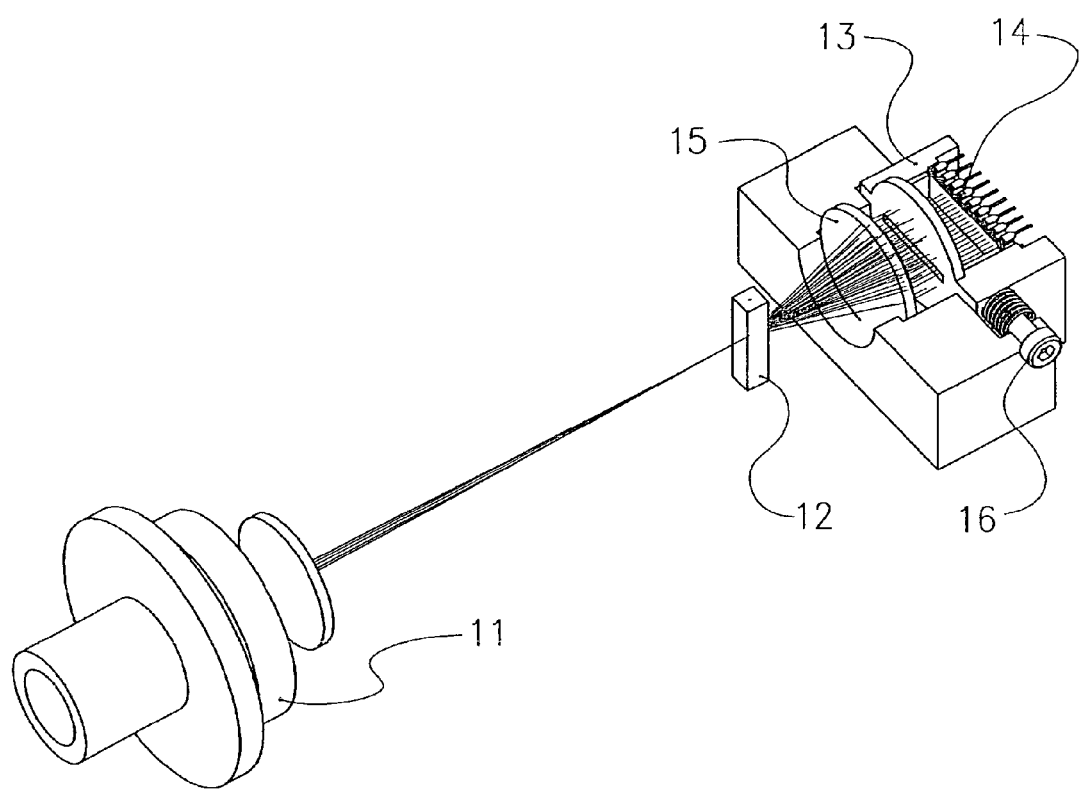
FIG. 1 shows a perspective view of a preferred embodiment of the device according to the present invention.

With reference to the accompanying FIG. 1, a perspective view of a preferred embodiment of the device according to the present invention is shown, in which the following component parts may be identified: a LED light source 11; a flow cell 12 (e.g. formed by means of a cell, model 151-051, made by Helma Italia Srl), a light collecting lens 15; a light detector 14 (e.g. formed by means of a CCD type detector), the supporting element 13 for said detector 14; means for adjusting the position of said supporting element 13, preferably comprising a position adjusting screw 16.

Said LED light source 11 comprises a light emitting element formed, for example, by means of a lamp, an individual or multiple LED, a laser diode or an ion laser device—adapted to emit a light beam and one or more lens forming the optical system to concentrate and focus said beam inside said flow cell 12, specifically on the particles carried by the conveying solution flow. Said light detector 14 preferably comprises at least five detector elements consisting for example of separate photodiodes.

With reference to FIGS. 2a, 2b and 2c, the parts forming the device according to the present invention are discriminated. The following elements are shown in greater detail: said supporting element 13 is adapted to move said detector 14 in a substantially orthogonal direction to the laser light beam entering said flow cell 12, by acting on said position adjusting screw 16.

By means of said convex-type, light collecting lens 15 focused in the centre of said flow cell 12, the various light beams consisting of the illuminating light beam and the scattering light beams originated by the particle transiting in said flow cell 12, are made parallel and filtered by the diaphragm or spatial filter consisting of a slot 18 belonging to a preferred embodiment of said detector-holder element 13, and thus impact on said light detector 14 adapted to convert the photon energy into electric current.

Specifically, in the accompanying FIGS. 2b and 2c, a perspective view of the device in accordance with the present invention is shown under a measuring condition: the focused beam 17, exiting from said flow cell 12, in the absence of particles which may divert it, is converted into a parallel ray beam 19 by said light collecting lens 15 and the fraction of said beam 19 which crosses said slot 18 illuminates said light detector, preferably of CCD type 14, in a point which depends on machining tolerances of the mechanical parts of the system, optical alignment tolerances of said light source 11, and said lens 15, as well as the flow position inside said flow cell 12.

Figure 3:
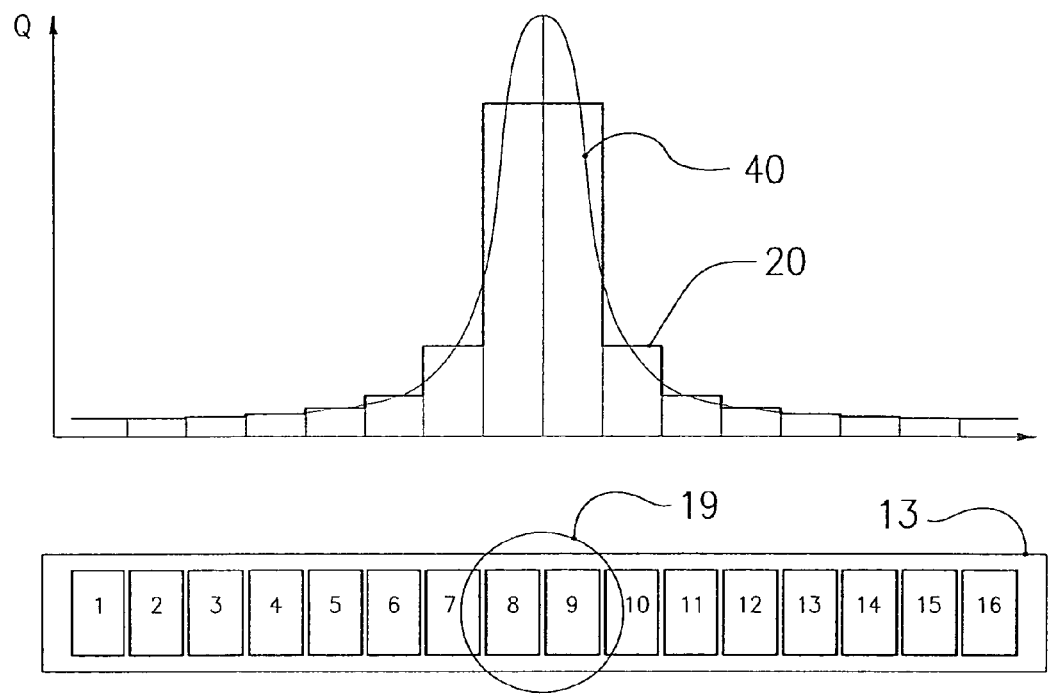
FIGS. 3 and 4 show a front view of the system comprising 16 photodiodes, 0.9×1.45 mm in size, which are the input photodetector elements of said CCD type light detector 14. The area 19 of the parallel ray beam which illuminates said photodetector elements is shown by a circle.

The accompanying FIG. 3 shows a front view of the system comprising sixteen photodiodes, 0.9×1.45 mm in size, which are the input photodetector elements of said CCD-type light detector 14. Furthermore, the area 19 of the parallel ray beam which illuminates said photodetector elements is shown by a circle.

During the step of aligning operated by the device in accordance with the present invention, the rotation of said position adjusting screw 16 allows to move said supporting element 13 carrying said lens 15 and said CCD-type light detector 14: thereby, all the previously listed tolerances may be compensated for. Said position adjusting screw 16 may be manually rotated, for example when testing the device at the factory or in case of its first use, so as to remedy manufacturing tolerances of the components employed and avoid the preventive screening of the components which would be very costly, or may be automatically rotated by means of an automatic system, preferably of the servo-assisted type, comprising an electric motor associated with said adjusting screw 16, driving means for said electric motor and control means associated with said driving means. The presence of said automatic servo-assisted system allows to carry out the calibration before each other measurement so as to compensate for the negative influence on the measurement result which could be caused by possible fluctuations of the external variables.

Specifically, if the beam 19 exiting from the lens 15 is wider than the individual element of said CCD-type light detector 14, said beam may be aligned with two adjacent elements close to the centre, and for example in the case of the CCD detector, model S4111-16Q/-16R (formed by 16 separate photodiodes, 0.9×1.45 mm in size, with active area 15.9× 1.45 mm, including 0.1 mm gaps between diodes), it may be moved straddling the elements 7 and 8, as shown in the accompanying FIG. 3.

Figure 4:
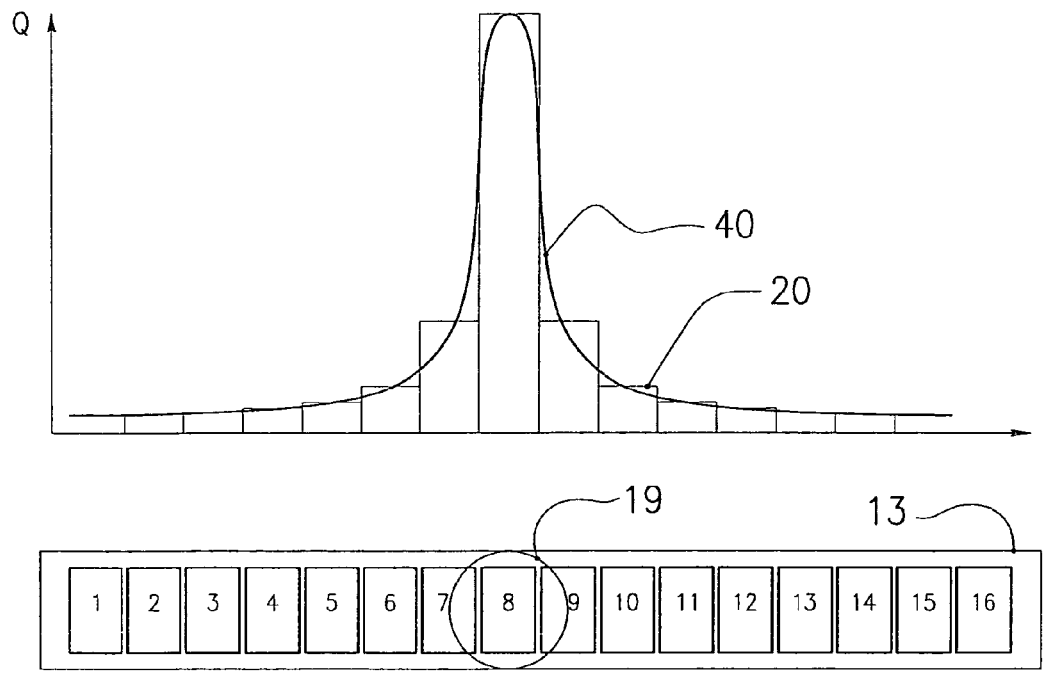

On the other hand, if the width of the beam exiting from the lens 15 is comparable with the individual element of said CCD-type light detector 14, said beam may be aligned with an individual central element, and specifically—in the case of the CCD detector, model S4111-16Q/-16R—with the element 8 as shown in the accompanying FIG. 4.

If the element 7 is only illuminated, the photoelectric response of the two adjacent elements 6 and 8 is controlled, by acting on said adjusting screw 16 to obtain equal electric signals; if the two elements 7 and 8 are illuminated, the adjustment is carried out by balancing the electric signals of the elements 7 and 8. Again with reference to the accompanying FIGS. 3 and 4, the width of the photoelectric signal Q of the individual elements is represented by a broken line 20 from which the continuous interpolating line 40 is extracted; the value of said photoelectric signal Q is about zero in the non-illuminated elements, the width increasing proportionally to the illumination.

Under the operative conditions of the device according to the present invention, the carrier solution which flows in said flow cell 12 drags the cells to be analyzed, and the concentration of the solution is adjusted by dilution so as to ensure the passage of only one cell at a time with a large gap between two subsequent cells, so as to generate a signal which is characteristic to each individual cell. The motion of the cell inside said flow cell 12 leads to intercept the beam itself, thus causing a complex light reflection and refraction phenomenon: the part reflected on the membrane surface of the cell is known as scattered light, while the refracted part originates from the light which crosses the cell and is attenuated due to the absorption and a possible further scattering phenomenon by nucleated elements. Scattered light is subjected to multiple angular deviations mathematically described by Mie's Law which, in clinical cytometry analysis technique, provides information correlated to cell diameter and biochemical membrane features; therefore, the quantitative combination of the light reflected under different angles produced by the individual cell allows to identify the type of cell sub-population to which it belongs.

The scattering signal collection apparatuses belonging to the state of the art and described in literature use detectors providing information on the amount of diverted light within four angles between 1 and 20 degrees. By employing a multiple N-element detector—where in a first preferred embodiment of the present invention N is at least equal to five, and in a second preferred embodiment shown in the accompanying FIGS. 6 and 7, is equal to 16—the device object of the present invention allows to measure up to N scattering light values which energize each element of the detector, the electric signal of which is the integral of said lights within the angular diversion specific for each element, and thus in the illustrated case, for each side for a total of 14 scattering values, in addition to the non-diverted light value.

Figure 6:
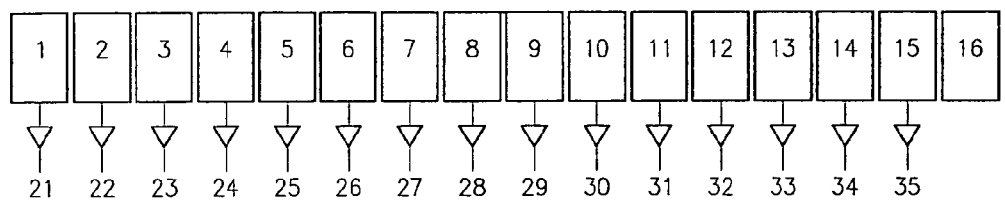
FIG. 6 shows the charge amplifiers 21-35 connected to the individual photodetector elements in a preferred embodiment of the device according to the present invention.

In the accompanying FIG. 6, the charge amplifiers 21-35 are shown connected to the individual photodetector elements in a preferred embodiment of the invention, which produced the output signals allowing to plot the stepped response feature 20 shown in FIG. 4.

By directly interconnecting the individual photodetectors employed in the device according to the present invention, various combinations of the involved signals may be obtained.

Figure 7:
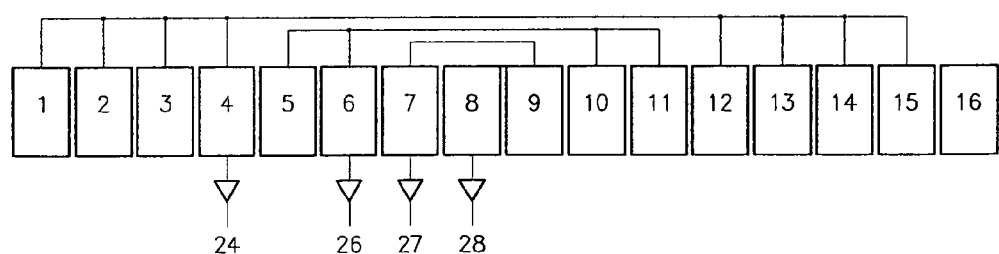
FIG. 7 shows a particular embodiment of the present invention which is a reduced solution employing four amplifiers only.
Figure 8:
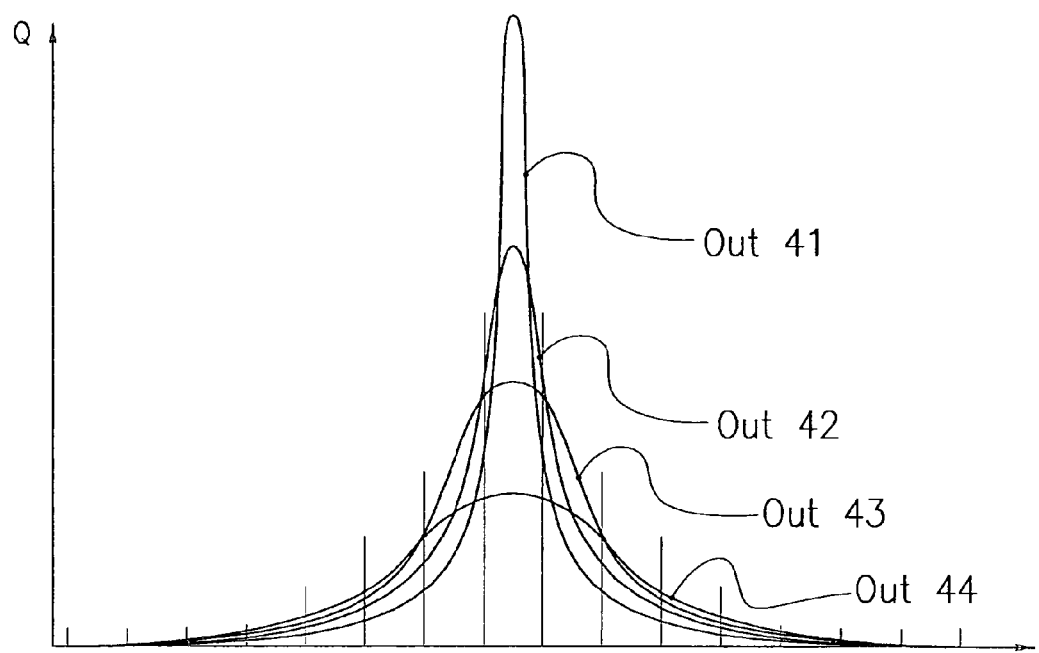
FIGS. 8 shows the interpolated output signals 41, 42, 43, 44 of the individual amplifiers 28, 27, 26, 24 of the type shown in FIG. 7.

By way of non-limitative example of the object of the present invention, FIG. 7 shows a particular embodiment of the present invention which is a reduced solution employing only 4 amplifiers, provides the electric connection between said photodetector elements, and provides the same information reduced to 4 angular scattering diversions intended for the already mentioned prior systems. FIG. 8 shows the interpolated output signals 41, 42, 43, 44 of the individual amplifiers 28, 27, 26, 24.

Figure 5:
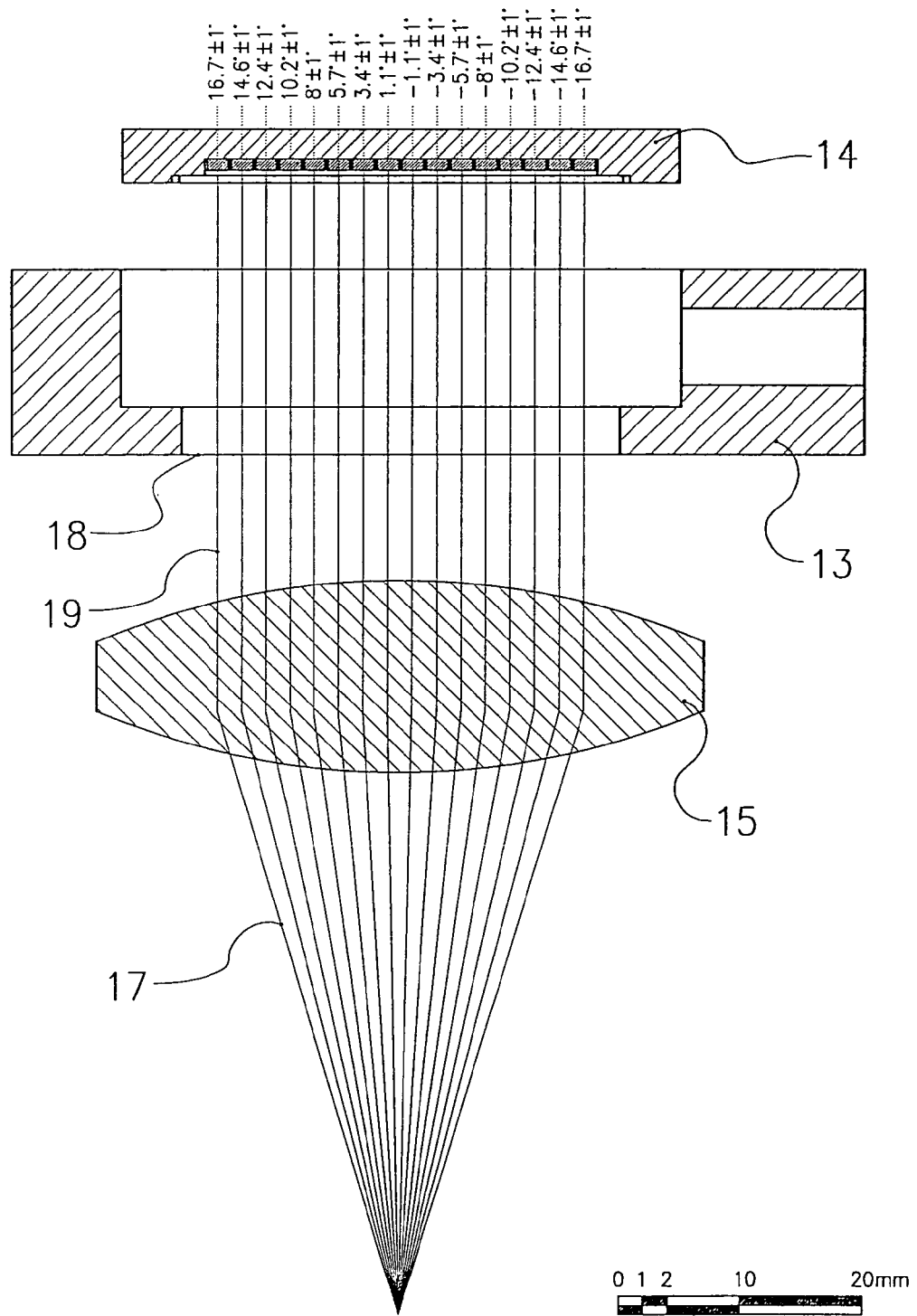
FIG. 5 shows the architecture of a preferred embodiment of the device according to the present invention.

On the other hand, by exploiting all the signals as in the configuration shown in FIG. 5, the various value sequences of the photoelectric signal Q of each photodetector element, corresponding to a certain cell type, may be identified by identifying the characteristic signature thereof, thus improving the attribution of the cells according to the class to which they belong.

Figure 9:
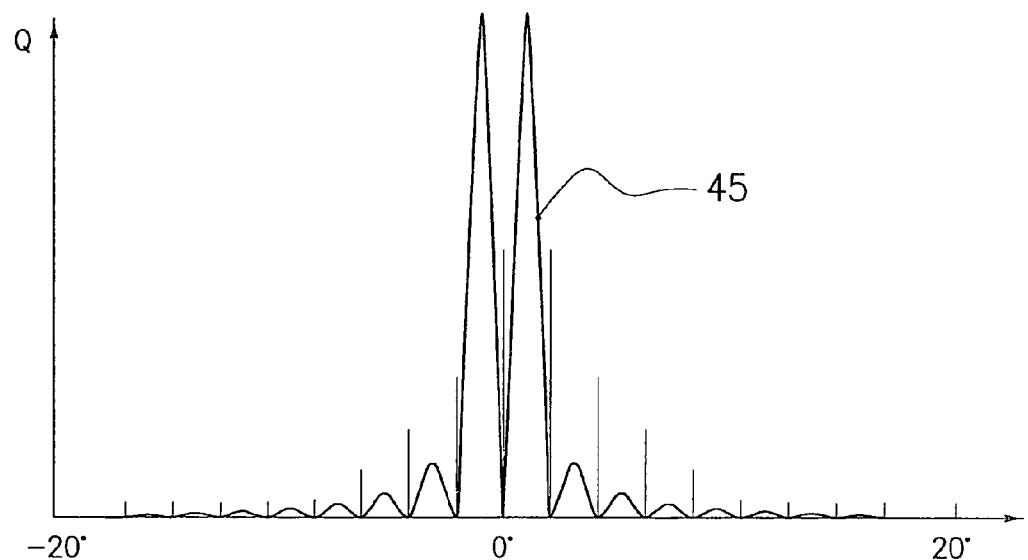
FIG. 9 shows the angular distribution of the scattering light on a latex particle having a diameter of 10 micrometers.

By way of example, the accompanying FIG. 9 shows the angular distribution of the scattering light on a latex particle having a diameter of 10 micrometers, calculated according to Mie's Law, which corresponds to the scattering light of the cellular membrane of a human lymphocyte-type cell: as shown, the phenomenon appears as a light intensity modulation, and the step of intensity distribution varies according to cell size and membrane and nucleus features of the various cells.

The fine analysis of light distribution at different angles allows to more easily recognize the cell under examination and aggregate it to the class to which it belongs. The signature of the cell thus results from the binary sequence of high-low signals of the various photodetector elements and electric outputs of the corresponding amplifiers.

Another possible analysis by virtue of the use of the device according to the present invention arises from the comparison of the signals of pairs of symmetric photodetector element with respect to the optical axis: for example, the second element on the right and on the left of the central element (consisting of an individual photodetector in the condition shown in FIG. 4, and instead of two photodetector in the condition shown in FIG. 3) could present the same signal in the case of optically symmetric cells, or different signals for optically asymmetric cells.

The invention claimed is:

1. An optical device for compensating scattering light signals, comprising: a light source, a flow cell, a light collecting lens, a light detector, a supporting element associated with said detector, adjusting means for the position of said supporting element, a slot, associated with said supporting element, and adapted to shape the focused beam exiting from said flow cell into a substantially planar beam, characterised in that said slot is arranged with its greater dimension substantially perpendicular to the cell flow direction inside said flow cell.

2. The device according to claim 1, wherein said light source further comprises one or more lenses adapted to concentrate and focus said beam within said flow cell, and specifically onto the particles dragged by the flow of the carrier solution.

3. The device according to claim 1, wherein said supporting element is further adapted to displace said detector in a substantially orthogonal direction to the laser light beam entering said flow cell.

4. The device according to claim 1, wherein said light source comprises a light emitting element selected from the group consisting of bulbs, individual or multiple LED diodes, laser diodes, and ion laser devices.

5. The device according to claim 1, wherein said light collecting lens is of the convex type and focused in the center of said flow cell.

6. The device according to claim 1, wherein said light detector comprises at least five detector elements selected from the group consisting of silicon photodiodes, APD-type photodiodes, and CCD-type photodiodes.

7. The device according to claim 1, wherein said light detector further comprises at least one charge amplifier associated with said at least five detector elements.

8. The device according to claim 6, wherein said light detector comprises sixteen detector elements and sixteen charge amplifier elements associated with said sixteen detector elements.

9. The device according to claim 1, wherein said adjusting means for the position of said supporting element comprises at least one adjusting screw.

10. The device according to claim 9, wherein it comprises an electric motor associated with said adjusting screw, driving means for said electric motor and control means associated with said driving means.

11. The device according to claim 1, wherein said light detector comprises N detector elements associated with a lower number of amplifiers.

12. The method of compensating scattering light signals with the device according to claim 1, comprising the following steps:
   a) comparing the dimensions of the light beam exiting from the flow cell of the device with the dimensions of the individual detector elements forming the employed light detector;
   b) if said light beam is larger in size than said individual elements, then said beam is aligned with two adjacent detector elements, otherwise the method proceeds with step d);
   c) changing the position of said light detector so that the photoelectric responses of the two adjacent detector elements illuminated in the previous step are the same, and the procedure ends;
   d) aligning said beam with a detector element; and,
   e) changing the position of said light detector so that the photoelectric responses of the two detector elements adjacent to the element illuminated in the previous step are the same, and the procedure ends.

* * * * *